(12) United States Patent
Weinberger et al.

(10) Patent No.: US 8,945,511 B2
(45) Date of Patent: Feb. 3, 2015

(54) SENSITIVE METHODS FOR DETECTING THE PRESENCE OF CANCER ASSOCIATED WITH THE OVER-EXPRESSION OF GALECTIN-3 USING BIOMARKERS DERIVED FROM GALECTIN-3

(76) Inventors: Paul Weinberger, Augusta, GA (US); John M. Koomen, Tampa, FL (US); Willam Shelley Dynan, Augusta, GA (US); David James Terris, Martinez, GA (US); Mark Asher Markley, Rochester, NY (US)

( * ) Notice: Subject to any disclaimer, the term of this patent is extended or adjusted under 35 U.S.C. 154(b) by 460 days.

(21) Appl. No.: 12/822,763

(22) Filed: Jun. 24, 2010

(65) Prior Publication Data
US 2012/0083011 A1   Apr. 5, 2012

Related U.S. Application Data

(60) Provisional application No. 61/269,421, filed on Jun. 25, 2009.

(51) Int. Cl.
| | | |
|---|---|---|
| *A61K 49/00* | (2006.01) | |
| *A61K 38/18* | (2006.01) | |
| *A61K 9/00* | (2006.01) | |
| *A61K 9/06* | (2006.01) | |
| *A61K 9/51* | (2006.01) | |
| *A61K 47/20* | (2006.01) | |
| *A61K 47/42* | (2006.01) | |
| *A61K 38/17* | (2006.01) | |

(52) U.S. Cl.
CPC ............... *A61K 38/18* (2013.01); *A61K 9/0019* (2013.01); *A61K 9/0092* (2013.01); *A61K 9/06* (2013.01); *A61K 9/5153* (2013.01); *A61K 47/20* (2013.01); *A61K 47/42* (2013.01); *A61K 38/179* (2013.01)
USPC .......................................................... 424/9.1

(58) Field of Classification Search
CPC ... A61K 38/179; A61K 38/18; A61K 9/5153; A61K 47/42; G01N 24/00
See application file for complete search history.

(56) References Cited

U.S. PATENT DOCUMENTS

| | | | |
|---|---|---|---|
| 5,038,039 | A | 8/1991 | Wong et al. |
| 5,555,885 | A | 9/1996 | Chance |
| 6,870,620 | B2 | 3/2005 | Faupel et al. |
| 6,975,899 | B2 | 12/2005 | Faupel et al. |
| 2003/0003465 | A1 | 1/2003 | Little et al. |
| 2004/0049107 | A1 | 3/2004 | Chutjian et al. |
| 2005/0074793 | A1 | 4/2005 | Wilson et al. |
| 2005/0196773 | A1 | 9/2005 | Sidransky et al. |
| 2007/0054345 | A1* | 3/2007 | Hunter ............................ 435/23 |
| 2008/0003971 | A1 | 1/2008 | Vaisanen |
| 2008/0227098 | A1 | 9/2008 | Krajewska et al. |

FOREIGN PATENT DOCUMENTS

| | | |
|---|---|---|
| WO | 03087793 | 10/2003 |
| WO | 2004021009 | 3/2004 |
| WO | 2006020302 | 2/2006 |

OTHER PUBLICATIONS

Inohara et al, Expression of galectin-3 in fine-needle aspirates as a diagnostic marker differentiating benign from malignant thyroid neoplasms Cancer vol. 85, Issue 11, pp. 2475-2484, Jun. 1, 1999.*
Laiko et al, Identification of a role for Shiga toxin (STX1) in enterohemorrhagic colitis includes increased TNF alpha and downregulation of galectin-3. Gastroenterology, (Apr. 2006) vol. 130, No. 4, Suppl. 2, pp. A367.*
Janecki et al, A multiple reaction monitoring method for absolute quantification of the human liver alcohol dehydrogenase ADH1C1 isoenzyme. Analytical Biochemistry 369 (2007) 18-26.*
USPTO in house download of U.S. Appl. No. 61/269,421, Weinberger, filed as an affidavit in the instant application on Dec. 6, 2012.*
ExPASy Peptide Cutter, analysis of trypsin cleavage sites for human galactin-3 (AAA88086.1). Performed Jul. 17, 2014.*
Henderson et al, The regulation of inflammation by galectin-3. Immunol Rev. Jul. 2009;230(1):160-71.*
de Boer et al, Galectin-3 in Cardiac Remodeling and Heart Failure. Curr Heart Fail Rep (2010) 7:1-8.*

* cited by examiner

*Primary Examiner* — Sheridan Swope
(74) *Attorney, Agent, or Firm* — Gardner Groff Greenwald & Villanueva, PC

(57) ABSTRACT

Described herein are sensitive methods for determining if a subject has cancer. The methods generally involve quantifying the amount of one or more biomarkers derived from Galectin-3 in a biological sample from the subject by mass spectrometry, wherein an increase in the amount of one or more biomarkers in the biological sample as compared to a control is an indication of the presence of cancer in the subject.

5 Claims, 5 Drawing Sheets

| parent ion sequence | peptide m/z | transition ions | |
|---|---|---|---|
| [H]IALDFQR[OH] | 431.743 | 565.272 | y4 |
| | | 678.356 | y5 |
| | | 749.394 | y6 |
| | | 450.245 | y3 |
| [H]GNDVAFHFNPR[OH] | 637.307 | 888.447 | y7 |
| | | 817.41 | y6 |
| | | 670.341 | y5 |
| | | 533.283 | y4 |
| [H]LDNNWGR[OH] | 437.712 | 761.332 | y6 |
| | | 646.305 | y5 |
| | | 533.262 | y4 |
| | | 418.219 | y3 |
| [H]QVLVEPDHFK[OH] | 662.867 | 1083.583 | y9 |
| | | 84.514 | y8 |
| | | 871.43 | y7 |
| | | 772.362 | y6 |
| | | 643.319 | y5 |

FIG. 1

SENSITIVE METHODS FOR DETECTING THE PRESENCE OF CANCER ASSOCIATED WITH THE OVER-EXPRESSION OF GALECTIN-3 USING BIOMARKERS DERIVED FROM GALECTIN-3

CROSS REFERENCE TO RELATED APPLICATIONS

This application claims priority upon U.S. provisional application Ser. No. 61/269,421, filed Jun. 25, 2009. This application is hereby incorporated by reference in its entirety for all of its teachings.

CROSS REFERENCE TO SEQUENCE LISTING

Peptides described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

In general, the ability to detect cancer in a sensitive manner is critical to proper diagnosis and subsequent treatment. Although significant to all forms of cancer, sensitive detection of thyroid cancer is of particular importance. The incidence of thyroid cancer is increasing, with over 19,000 new cases in the United States per year. Thyroid nodules are extremely common in the general population. The discernment of which nodules require surgical excision is of paramount importance, as only 5% of nodules are malignant. In current clinical practice, this determination involves the isolation and use fine needle aspirates (FNA) followed by histological analysis. This test is sensitive and specific for the majority of thyroid cancers. However, when cytological specimens are graded "non-diagnostic" (10-15%) or as "follicular neoplasm" (5-10%), this usually results in surgical removal by hemithyroidectomy to determine carcinoma from benign growth.

Enzyme Linked Immunosorbent Assay (ELISA) is a biochemical technique used in biochemistry, clinical chemistry, and immunology to detect the presence of an antigen in a specific sample. In ELISA an unknown amount of antigen is affixed to a surface, and then a specific antibody is washed over the surface so that it can bind to the antigen. This antibody is linked to an enzyme, and in the final step a substance is added that the enzyme can convert to some detectable signal. Galectin-3, a protein that is present in elevated amounts in patients having thyroid malignancies and other cancers, has been detected using these kits in a variety of complex biologic samples including FNA. These kits typically use a rabbit derived antigalectin-3 linked to a horseradish peroxidase enzyme, and a biotin conjugated label molecule. The detection of Galectin-3 in biologic fluids using commercially available ELISA kits has yielded mixed results. Additionally, ELISA may not be applicable to other biological samples such as serum. Finally, ELISA cannot detect multiple protein or peptide biomarkers, which can provide more sensitive detection that ultimately results in better diagnosis of cancer.

SUMMARY

Described herein are sensitive methods for determining if a subject has cancer. The methods generally involve quantifying the amount of one or more biomarkers derived from Galectin-3 in a biological sample from the subject by mass spectrometry, wherein an increase in the amount of one or more biomarkers in the biological sample as compared to a control is an indication of the presence of cancer in the subject. The validation of reliable biomarkers predictive of malignancy permits the detection of cancer using a non-invasive test, and obviates the need for hemithyroidectomy in the case of benign growth. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 1 shows the summary of results from LC-MS/MS analysis of SEQ ID NOS 1-4 and selected transitions chosen based on high fragment ion signal and high fragment ion m/z.

DETAILED DESCRIPTION

Figure 2:
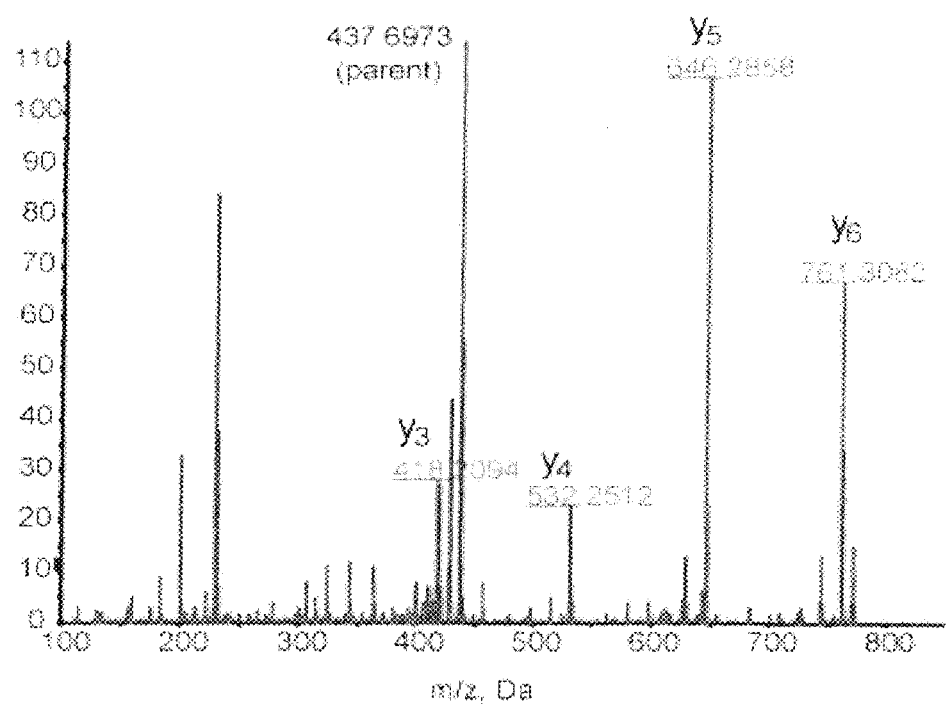
FIG. 2 shows a representative mass spectrum of SEQ ID NO 3.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a biomarker" includes mixtures of two or more such biomarkers, and the like.

"Optional" or "optionally" means that the subsequently described event or circumstance can or cannot occur, and that the description includes instances where the event or circumstance occurs and instances where it does not.

As used herein, "subject" refers to a human that may or may not have cancer or who is suspected of having cancer.

As used herein, the term "peptide" may be used to refer to a natural or synthetic molecule comprising two or more amino acids linked by the carboxyl group of one amino acid to the alpha amino group of another. The peptide is not limited by length, and thus "peptide" can include polypeptides and proteins.

As used herein, the term "isolated," with respect to peptides, refers to material that has been removed from its original environment, if the material is naturally occurring. For example, a naturally-occurring peptide present in a living animal is not isolated, but the same peptide, which is separated from some or all of the coexisting materials in the natural system, is isolated. Such isolated peptide could be part of a composition and still be isolated in that the composition is not part of its natural environment. An "isolated" peptide also includes material that is synthesized or produced by recombinant DNA technology.

As used herein, the term "about" is used to provide flexibility to a numerical range endpoint by providing that a given value may be "a little above" or "a little below" the endpoint without affecting the desired result.

When describing variants in proteins or peptides, the term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 65%, 70%, 75%, 80%, 85%, 90%, 95%, 96%, 97%, 98%, or 99% homology to a reference sequence.

The terms "homology," "identity" and "similarity" refer to the degree of sequence similarity between two peptides. Homology and identity can each be determined by comparing a position in each sequence which can be aligned for purposes of comparison. For example, it is based upon using a standard homology software in the default position, such as BLAST, version 2.2.14. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectfully. A sequence which is "unrelated" or "non-homologous" shares less than 40% identity, though preferably less than 25% identity with the sequences as disclosed herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Described herein are methods for the sensitive detection of cancer in a subject. The methods generally involve quantifying the amount of one or more biomarkers derived from Galectin-3 in a biological sample from the subject by mass spectroscopy, wherein an increase in the amount of one or more biomarkers in the biological sample as compared to a control is an indication of the presence of cancer in the subject. The term "biomarkers" as used herein refers to one or more peptide fragments derived from the beta-galactoside-binding protein Galectin-3. Methods for producing the biomarkers from Galectin-3 are provided below. Not wishing to be bound by theory, Galectin-3 regulates biological processes including cell adhesion, migration, cell growth, tumor progression, metastasis and apoptosis. Galectin-3 inhibits nitrogen free radical-mediated apoptosis, improves mitochondrial stability in the face of impending cell death, and also inhibits apoptosis induced by loss of cell adhesion. Thus, in one aspect, the methods described herein involve the detection and quantification of one or more peptide fragments of Galectin-3 to determine if a subject has cancer. The methods are described in detail below.

The first step involves obtaining a biological sample from a subject suspected of having cancer. In one aspect, the cancer is associated with an over-expression of Galectin-3. In other words, a subject with cancer associated with an over-expression of Galectin-3 is likely to exhibit or possess increased amounts of Galectin-3 relative to a subject that does not have cancer. Examples of cancers associated with the over-expression of Galectin-3 include, but are not limited to, thyroid cancer, head cancer, colon cancer, gastric cancer, pancreatic cancer, or cholangiocarcinoma (i.e., cancer of the gall bladder).

The biological sample used in the methods described herein can in some aspects be any bodily fluid, tissue, or cells from the subject in which the assaying for the levels of the biomarkers is desired. Examples of biological samples useful herein include, but are not limited to, thyroid tissue, serum, plasma, blood, urine, cerebrospinal fluid, amniotic fluid, synovial fluid, cervical vaginal fluid, lavage fluid, an aspirate, common bile duct aspirate, or any combination thereof. In one aspect, the methods described herein are useful for fine needle aspirates for the clinical evaluation of palpable and nonpalpable thyroid nodules. For example, using a 22-gauge needle, 4 to 6 passes are made into the suspect nodule without exiting the skin. The material is subsequently aspirated into storage medium and transported for evaluation by a certified histopathologist.

Depending upon the type of sample that is collected and used, Galectin-3 as well as other proteins and cellular components can be released from cells present in the sample using techniques known in the art. For example, the cells can be exposed to one or more cell lysing solutions to release the cellular components to produce a lysate. The selection of the lysate will vary depending upon the sample and nature of the isolated cells. In one aspect, when the sample is a fine needle aspirate, the needle is washed in order to remove residual cells in the needle, the washing is subsequently centrifuged in order to collect the cells to be lysed. In other aspects, when the sample is serum, the serum is centrifuged to remove white- and red-blood cells, and the serum is ready for further processing. After processing has been performed, additional steps can be performed to isolate and purify Galectin-3.

After isolating Galectin-3 from the cells, the sample is contacted with one or more enzymes that can digest Galectin-3 to produce two or more peptide fragments (i.e., biomarkers). The selection and amount of the enzyme can vary. Upon digestion of Galectin-3 with trypsin, the following biomarkers are produced (Table 1).

TABLE 1

| SEQ ID NO | Sequence | $[M + 2H]^{2+}$ m/z |
|---|---|---|
| SEQ ID NO 1 | IALDFQR | 431.74 |
| SEQ ID NO 2 | GNDVAFHFNPR | 637.31 |
| SEQ ID NO 3 | LDNNWGR | 437.71 |
| SEQ ID NO 4 | IQVLVEPDHFK | 662.87 |

The biomarkers listed in Table 1 can be purified using techniques known in the art or, in the alternative synthetically prepared using techniques known in the art. For example, solid-phase peptide synthesis is one such method for synthetically creating peptides. Small solid beads are treated with linkers on which peptide chains can be subsequently built. The peptide is thus bound on the solid-phase and immobilized as subsequent reagents are flushed away during washing steps. Repeated cycles of coupling (carboxyl group of one amino acid to the amino group of another) followed by washings thus allow propagation of the peptide one amino acid at a time. In other aspects, labeled peptides can be created by inclusion of a stable isotope labeled amino acid containing carbon-13 and nitrogen-15 or by substituting one amino acid with a different molecular weight for the original (native) amino acid. Other potential methods include expression in a bacterial plasmid model by incorporating DNA encoding the peptide sequence of interest into a bacterial plasmid, infecting a recipient bacterial strain, and growing the bacteria to produce the peptide of interest.

After digestion of Galectin-3, the sample does not require additional processing and purification. At this point, an external control can be added to the sample containing the biomarker(s). For example, a control can be added to the sample containing the biomarker(s) at a known concentration. The level or amount of biomarker in the sample can then be compared to the level or amount of the same biomarker(s) present in a subject that does not have cancer with the same amount of control. Thus, an increase in the amount biomarker present in the sample from the subject compared to the amount present in a subject that does not have cancer can be an indicator that the subject has cancer. In one aspect, standard curves can be prepared based on different amounts of control used such that the amount of biomarker present in the sample can be evaluated against the curve to determine if the subject has cancer. In one aspect, the control can be a variant of any biomarker described and used herein. For example, the control has an amino acid sequence IALDFNR (SEQ ID NO 5) or LDNNWAR (SEQ ID NO 6). In this aspect, SEQ ID NO 5 and SEQ ID NO 6 are structurally identical to SEQ ID NO 1 and SEQ ID NO 3, respectively, with the exception of one amino acid in SEQ ID NO 1 or SEQ ID NO 3 was substituted for another amino acid. SEQ ID NO 5 and SEQ ID NO 6 can be synthesized using techniques know in the art. The concentration of the control can vary. In one aspect, the concentration of the control is from 0.1 to 100 fmol.

After the peptide internal standard (i.e., control) has been added to the sample, the relative amount of biomarker(s) is determined. The methods described herein use mass spectroscopy to quantify the amount of biomarker(s) at very low concentrations. For example, the methods described herein can detect the biomarker at concentrations as low as 20 attomoles. The sensitivity of the methods described herein is much greater compared to ELISA. For example, the lower limit of detection of ELISA is typically reported in the picogram range. As shown in the Examples, the methods described herein are several fold more sensitive (e.g., 100 attomoles corresponding to 0.0026 picograms).

Due to the complexity of the biological samples, the separation of liquid chromatography coupled to tandem mass spectrometry can be used to either identify or isolate the signals corresponding to Galectin-3 to enable quantitative measurements of the biomarkers. Thus, either LC-MS/MS or LC-MRM could be used herein.

In one aspect, multiple reaction monitoring (MRM) can be used to detect and quantify two or more biomarker(s) of interest. For example, a triple quadrupole mass spectrometer can be adjusted to specifically pass through the signal for the predicted collision fragments. Detected molecules can then be subjected to MS/MS sequencing for confirmation of specificity. Once a target biomarker having favorable MS flight characteristics is determined, heavy-isotope labeled peptide fragments can be created. These heavy peptides can be used as subsequent internal controls as discussed above for quantification of experimental results to known standards. The combination of a triple quadrupole and an ion trap allows the real-world application of MRM to complex biological samples. This system couples the high specificity of precursor ion scanning through a triple quadrupole, with the sensitivity of a high performance linear ion trap. When ions are detected in the highly selective precursor ion scan, the instrument automatically switches modes with less than a 700-ms delay, and performs an enhanced resolution scan to obtain peptide mass. This is then followed automatically by an MS/MS sequencing scan (afforded by the linear ion trap mode). This takes place in less than 5 s, making it feasible to study large numbers of highly complex samples. One key advantage of MRM is the ability to detect multiple biomarkers, where each biomarker can selectively pass through the first quadrupole, allowing near-simultaneous detection of many biomarkers. Thus, the methods described herein permit the analysis of a large panel of biomarkers (n=10 s to 100 s). This feature is not possible with current analytical techniques such as ELISA.

The methods described herein can sensitively detect the over-expression of Galectin-3 in a sample by quantifying the amount of peptide fragments (i.e, biomarkers) produced from Galectin-3. As discussed above, the over-expression of Galectin-3 has been associated with several types of cancer. Therefore, in one aspect, an increase in the amount of one or more biomarkers derived from Galectin-3 compared to a control is an indicator the subject has cancer. In one aspect, SEQ ID NOS 1-4 have been identified as biomarkers for the presence of cancer.

In some aspects, an increase or an overexpression in the amount of Galectin-3 (i.e., biomarkers) in the biological sample as compared to a negative control is an indication of the presence of cancer in the subject. In one aspect, the negative control is a protein extract that contains purified Galectin-7 protein. For example, the negative control can be purified Galectin-7 protein spiked in a background of Albumin.

Alternatively, an increase or an overexpression in the amount of Galectin-3 (i.e., biomarkers) in the biological sample as compared to a positive control is an indication of the presence of cancer in the subject. In one aspect, the positive control is a mixture Galectin-3 protein having a known concentration plus other proteins. In another aspect, the positive control is cell lysate from cell lines with high or low expression of Galectin-3. In one aspect, a representative population of "normal" patients without cancer, and patients known to have thyroid cancer will be selected. Samples will be processed as described above, and Galectin-3 concentrations determined for each. Various "cutpoints" can then be compared for the resultant sensitivity and specificity of predicting cancer correctly.

Also described herein are kits for determining if a subject has cancer. Such kits may be employed by hospitals, clinics, reference laboratories, doctor's offices, etc. to help make medical decisions and, if necessary, provide available therapies or interventions. Additionally, such kits may also allow the diagnosis, prognosis, or risk assessment of other medical conditions associated with cancer.

In one aspect, the kit comprises (1) a control comprising at least one variant of a biomarker derived from Galectin-3 and (2) a digestion enzyme. Any of the controls and digestion enzymes described herein can be used in the kit. The kit can include optional components such as buffer solution for the digestion enzyme, positive and/or negative controls, and additional diluents for dissolving the controls and/or diluting the test sample. The kits can also include instructions for the settings to be used in the mass spectrometer for obtaining data. In one aspect, the kit is composed of:

1) Synthetically created normal peptide (for creation of a standard curve). (e.g., SEQ ID NO 1).
2) Internal control for spiking per sample run, to allow standardization from run to run, and from sample to sample within each run (e.g., SEQ ID NO 5 at 5 fM).
3) Positive control protein extract from Hela cells containing a known concentration of Galectin-3 whole protein plus complex mixture of other proteins, allows confirmation of sensitivity.
4) Negative control protein extract containing purified Galectin-7 protein spiked in a background of Albumin.
5) Sample Diluent Solution for creating serial dilutions of #1 for standard curve, and for diluting test samples and positive/negative control samples.
6) Trypsin enzyme for digesting samples and positive/negative controls.
7) Digestion buffer for diluting the trypsin enzyme.
8) Settings for setting a triple-quadropole mass spectrometer for capturing data from the galectin-3 peptide fragments.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Using the known protein sequence of human Galectin-3 it was possible to generate MIDAS workflow methods via the MRM builder software tool (see FIG. 1). The MIDAS workflow allows the user to perform an information dependent acquisition (IDA) using our preselected precursor ion. The MRM driven IDA provides all of the advantages of MRM with high sensitivity, high signal to noise ration, and high selectivity. This program allows for the user to provide input in the form of the peptide sequence of a particular protein of interest and then allows the MRM to search for those peptides. Following MRM run on the sample and detection of the appropriate peptides, enhanced resolution (ER) scans were performed on each peak to obtain accurate charge and m/z information. For confirmation following this MS/MS can be performed thus providing additional validation of identify and quantification of sample (FIG. 2). The MRM builder script, upon entry of the desired protein sequence, automatically populates acquisition methods for detecting the predicted peptides. The tool determines a list of MRM transitions, calculates the proper collision energy, and builds an acquisition method. These acquisition methods were then used to specifically detect the peptide sequences corresponding to Galectin-3 in blank solution.

Figure 3:
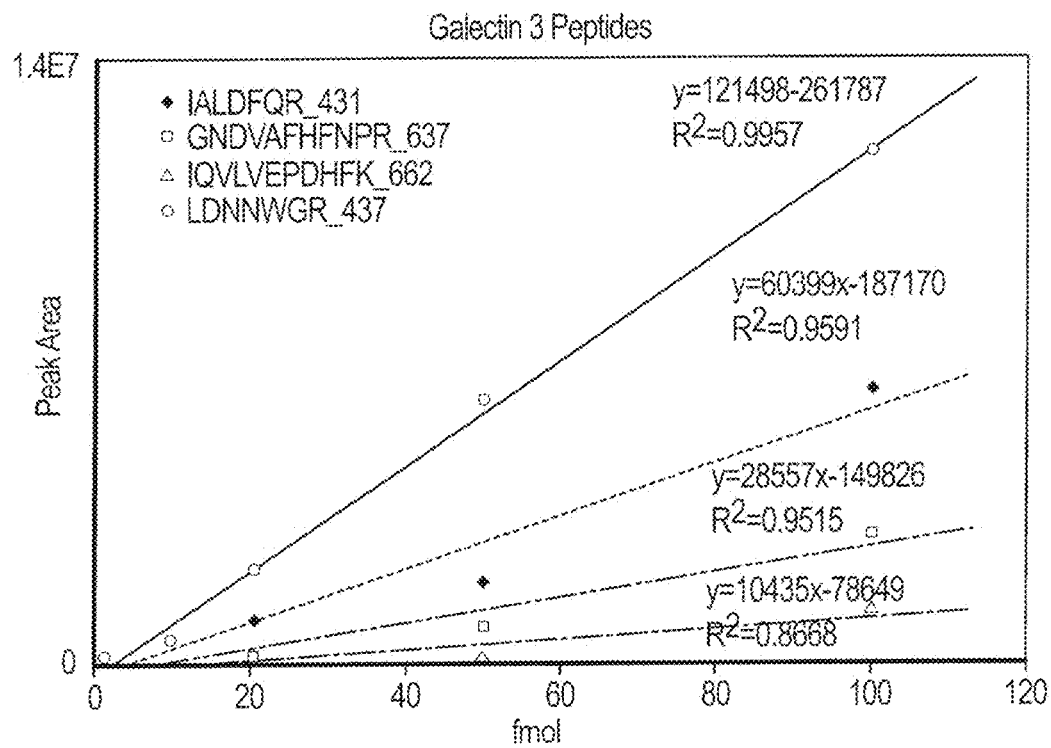
FIG. 3 shows a calibration curve based on 0.1 to 100 fmol injection of tryptic digest on LC column, where each point is mean of duplicates.
Figure 4:
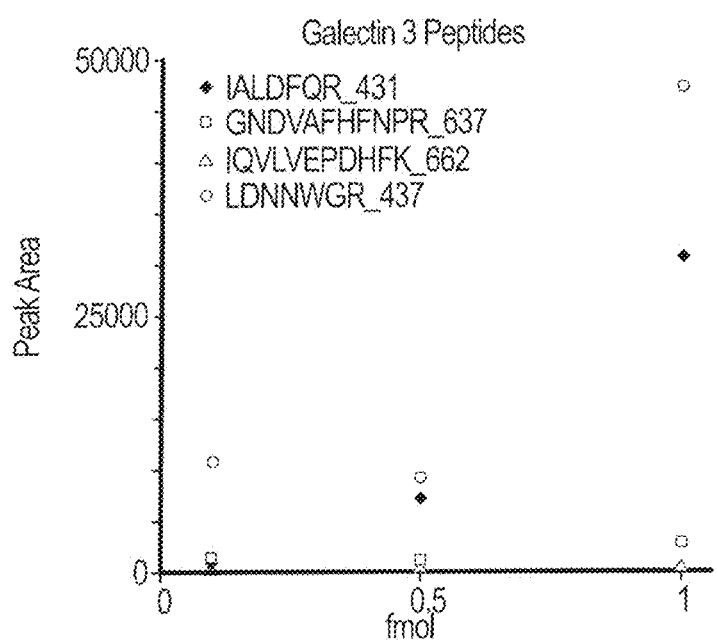
FIG. 4 shows a zoomed low-concentration region of curve for SEQ ID NOS 1-4.

Following creation of an appropriate acquisition model for candidate peptides corresponding to Galectin-3, the protein was subjected to denaturation and tryptic digestion. Approximately 50 ng of the protein was serially diluted and the dilutions were sequentially applied to the MRM. Detection of peptides corresponding to Galectin-3 was reliably demonstrated down to 100 attomoles or corresponding 0.0026 picograms (FIGS. 3 and 4).

Example 2

Isobaric peptide Internal Standards (IS) were made in order to quantitatively measure Galectin-3 levels. Specifically, SEQ ID NOS 5 and 6 were synthesized using standard solid phase FMOC chemistry. Wang resin (Novabiochem, Germany) served as the support to initiate peptide formation. Activator solvents for the amino acid coupling consisted of 150 mM N-Methylmorpholine in N-methylpyrrolidone (NMP) with 100 mM of O-benzotriazol-1-yl-N,N,N',N'-tetramethyluronium hexafluorophosphate (HBTU). Deprotection between couplings was achieved using 20% piperidine in NMP with 2% 1,8-diazabicyclo[5,4,0]undec-7-ene. Upon sequence completion, cleavage from the resin was performed using 95% TFA, 2.5% water, and 2.5% triisopropylsilane. Peptides were then precipitated in ice cold ethyl ether, washed twice, and resuspended in water prior to lyophilization. HPLC purification was performed on a semi-preparative system (U3000, Dionex, Sunnyvale, Calif.) using a C18 reverse phase column (TP 238, 250×10 mm, 10-15 mm particles, Grace Vydac, Deerfield, Ill.). Twenty minute gradients were run from 5% to 60% B solvent (A: 2% acetonitrile/0.1% formic acid; B: 90% acetonitrile/0.1% formic acid). Eluted peptides wee measured at 204 and 214 nanometer wavelengths and collected with automatic triggering (Foxy Jr, ISCO).

Figure 5:
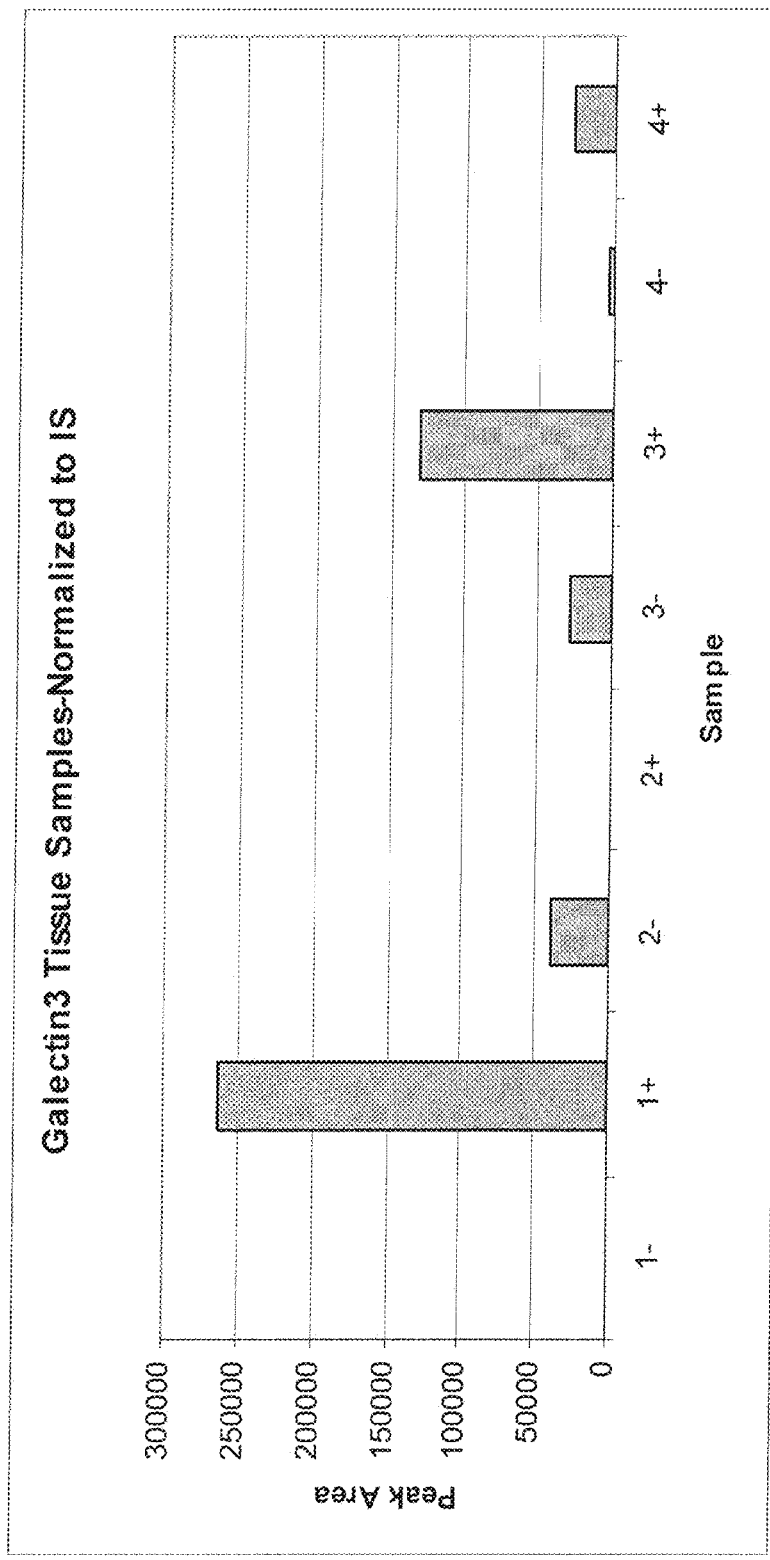
FIGS. 5 and 6 show replicate quantitative determinations (using isobaric-labelled internal standard peptides based on SEQ ID NO 3) of galectin-3 concentration within thyroid FNA samples from patients with (+) and without (−) thyroid cancer.
Figure 6:
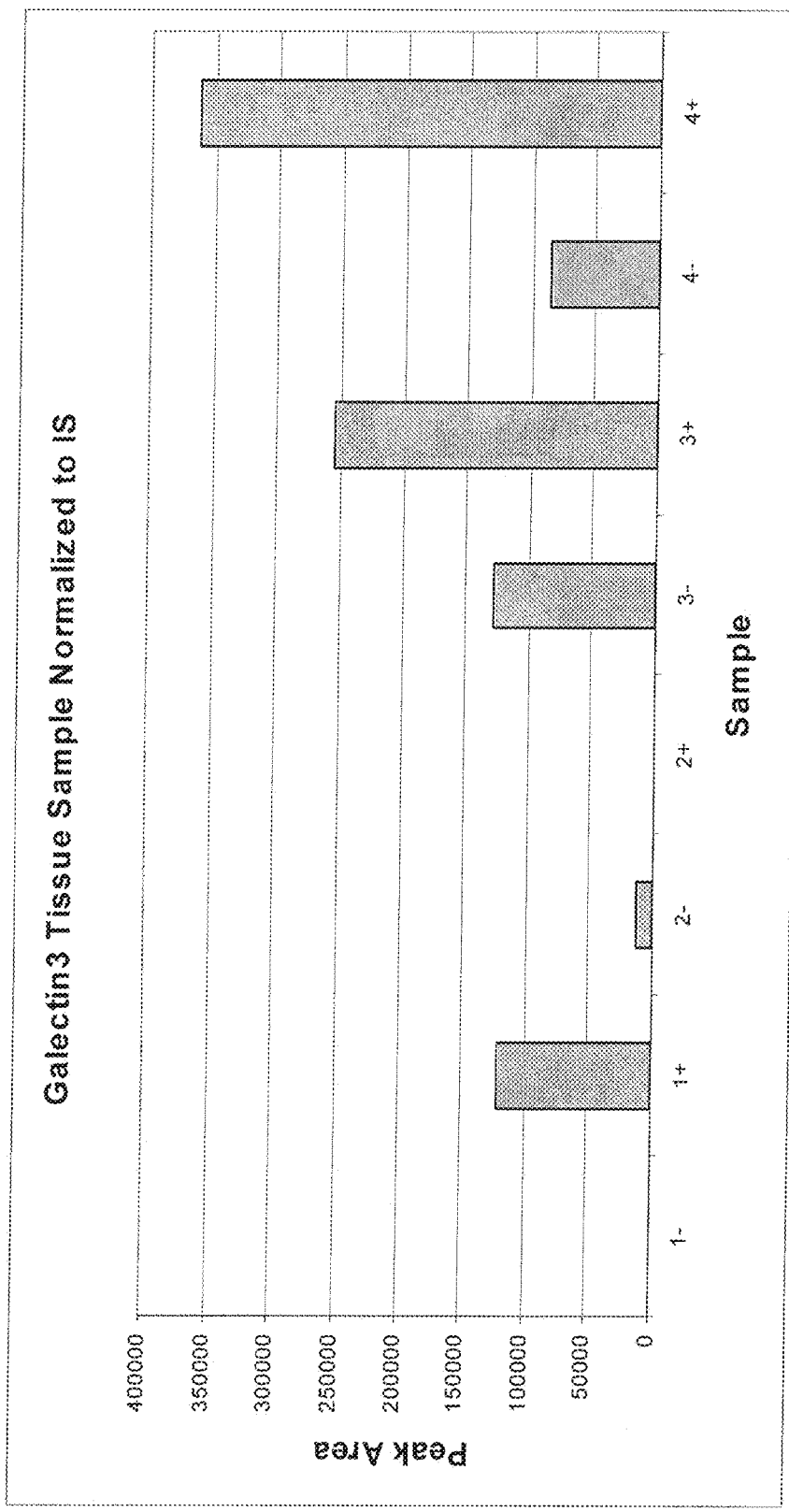

SEQ ID NO 5 exhibited the strongest signal. Thus, samples were spiked with 5 fmol of SEQ ID NO 5. Native peptide signals from the samples were normalized using the internal standard for comparison across the samples. FNA needle washings from 8 real patients (4 whose tumors were Galectin-3 non-expressors by immunohistochemistry (samples 1– to 4–), and three with Galectin-3 abundant expression (samples 1+ to 4+) (FIG. 5). Replicate runs were made using the standards and the previously described MRM assay (FIG. 6). Referring to FIGS. 5 and 6, the + samples clearly had a higher amount of SEQ ID NOS 1-4 compared to the (–)

samples. Thus, the use of MRM can be used to quantify a plurality of biomarkers derived from Galectin-3.

It is to be understood that the above-described compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements.

Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed:

1. A method for determining if a subject has thyroid cancer, the method comprising
   (a) contacting a thyroid aspirate derived from the subject comprising galectin-3 with trypsin to digest galectin-3 and produce one or more biomarkers selected from the group consisting of SEQ ID NO 1, SEQ ID NO 2, SEQ ID NO 3, SEQ ID NO 4, and any combination thereof,
   (b) adding a control biomarker to the thyroid aspirate, wherein the control biomarker is SEQ ID NO 5 or SEQ ID NO 6,
   (c) quantifying the amount of the biomarker in the thyroid aspirate by multiple reaction monitoring, and
   (d) comparing the amount of the biomarker in the thyroid aspirate to the amount of the same biomarker from a second thyroid aspirate from a subject that does not have thyroid cancer,
   wherein an increase in the amount of the biomarker in the thyroid aspirate as compared to the amount of the same biomarker from the second thyroid aspirate from the subject that does not have thyroid cancer is an indication of the presence of thyroid cancer in the subject.

2. The method of claim 1, wherein the biomarker is at least two peptides selected from the group consisting of SEQ ID NO 1, SEQ ID NO 2, SEQ ID NO 3, and SEQ ID NO 4.

3. The method of claim 1, wherein the thyroid aspirate is a fine needle aspirate.

4. The method of claim 1, wherein the biomarker can be quantified in an amount as low as 20 attomoles.

5. The method of claim 1, wherein the thyroid aspirate is a fine needle aspirate and the control marker is SEQ ID NO 5.

* * * * *

SEQUENCE LISTING

```
<160> NUMBER OF SEQ ID NOS: 6

<210> SEQ ID NO 1
<211> LENGTH: 7
<212> TYPE: PRT
<213> ORGANISM: Homo sapiens

<400> SEQUENCE: 1

Ile Ala Leu Asp Phe Gln Arg
1               5

<210> SEQ ID NO 2
<211> LENGTH: 11
<212> TYPE: PRT
<213> ORGANISM: Homo sapiens

<400> SEQUENCE: 2

Gly Asn Asp Val Ala Phe His Phe Asn Pro Arg
1               5                   10

<210> SEQ ID NO 3
<211> LENGTH: 7
<212> TYPE: PRT
<213> ORGANISM: Homo sapiens

<400> SEQUENCE: 3

Leu Asp Asn Asn Trp Gly Arg
1               5

<210> SEQ ID NO 4
<211> LENGTH: 11
<212> TYPE: PRT
<213> ORGANISM: Homo sapiens

<400> SEQUENCE: 4

Ile Gln Val Leu Val Glu Pro Asp His Phe Lys
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

Ile Ala Leu Asp Phe Asn Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide
```

```
<400> SEQUENCE: 6

Leu Asp Asn Asn Trp Ala Arg
1               5
```